(12) United States Patent
Aitta et al.

(10) Patent No.: US 6,689,377 B2
(45) Date of Patent: Feb. 10, 2004

(54) SOLID FORMIC ACID PRODUCT

(75) Inventors: Eero Aitta, Jokirinne (FI); Jouko Arvola, Oulu (FI); Pekka Johnson, Espoo (FI); Juha Kangastalo, Oulu (FI); Marjo Luoma, Oulu (FI); Ilkka Pollari, Espoo (FI)

(73) Assignee: Kemira Chemicals Oy, Helsinki (FI)

( * ) Notice: Subject to any disclaimer, the term of this patent is extended or adjusted under 35 U.S.C. 154(b) by 0 days.

(21) Appl. No.: 10/220,313

(22) PCT Filed: Feb. 28, 2001

(86) PCT No.: PCT/FI01/00200

§ 371 (c)(1),
(2), (4) Date: Oct. 23, 2002

(87) PCT Pub. No.: WO01/64050

PCT Pub. Date: Sep. 7, 2001

(65) Prior Publication Data

US 2003/0092768 A1 May 15, 2003

(30) Foreign Application Priority Data

Mar. 1, 2000 (FI) .............................................. 20000475

(51) Int. Cl.⁷ ........................... A23K 1/22; A61K 47/00; A61K 49/00; A01N 25/08; A01N 25/00

(52) U.S. Cl. ...................... 424/442; 424/9.31; 424/405; 424/409; 424/439

(58) Field of Search ................................ 424/9.31, 405, 424/409, 439, 442

(56) References Cited

FOREIGN PATENT DOCUMENTS

| EP | 0 009 366 | 4/1980 |
| EP | 0 411 827 A1 | 2/1991 |
| EP | 0 891 717 A1 | 6/1998 |
| WO | 99/00023 | 1/1999 |

OTHER PUBLICATIONS

CAB Accession No. 971412720, R. Schulenberg et al., "Adsorbed Organic Components", Landabbauforschung Volkenrode, Sonderheft, 1996, No. 169, pp. 290–294.

Primary Examiner—Jon P. Weber
Assistant Examiner—Kailash C. Srivastava
(74) Attorney, Agent, or Firm—Burns, Doane, Swecker & Mathis, L.L.P.

(57) ABSTRACT

The invention relates to a solid antimicrobial product suitable for the preservation of an organic material and for combating of detrimental microorganisms, as well as for pH control. The product contains, absorbed into a support a concentrated formic acid partly neutralized with gaseous ammonia, the water content of the formic acid being below 2% by weight. In addition, the invention comprises a method for preparing the product.

11 Claims, No Drawings

SOLID FORMIC ACID PRODUCT

FIELD OF THE INVENTION

The invention is directed to a solid antimicrobial product especially suited for the preservation of organic material and for combating detrimental microorganisms, as well as for pH control. The invention is also directed to a method for producing a solid antimicrobial.

BACKGROUND OF THE INVENTION

In the description of the background of the present invention that follows reference is made to certain structures and methods, however, such references should not necessarily be construed as an admission that these structures and methods qualify as prior art under the applicable statutory provisions. Applicants reserve the right to demonstrate that any of the referenced subject matter does not constitute prior art with regard to the present invention.

Aqueous solutions of formic acid are known to be strongly corrosive solutions. The handling and storage of such solutions requires acid-resistant materials. This is a problem in industrial processes and agriculture where feed preservative solutions that contain formic acid are used. Machinery and equipment coming into contact with the solutions are subject to corrosion. Thereby their useful life is shortened, which causes extra costs to the industry and farmers.

Attempts have been made to find a solution to the problem by adding to an aqueous solution of formic acid substances that reduce corrosion. From EP application 411 827 there is known a feed preservative solution that contains formic acid and octanoic acid, and additionally possibly propionic acid and ammonia. However, the publication contains no mention of what the reduced corrosive action is based on.

FI patent 61790 discloses an aqueous solution containing formic acid and a cation. The ratio of the acid to the cation is 2:1–4:1, calculated on the basis of the chemical equivalents, and the water content is 15–90%, indicated in percentages by weight.

International application WO-99/00023 presents, as a solution to the problem, the neutralization of an 85% aqueous solution of formic acid with a base, such as ammonia, at an acid to base cation ratio higher than four, calculated on the basis of the chemical equivalents.

According to one known method, an aqueous solution of a formic acid complex salt is absorbed into supports. In EP application 009 366, there is added as a stabilizing agent to a milk-containing animal feed a 75% aqueous solution of a complex salt, absorbed into a support, the aqueous solution containing, for example, ammonium ions and formic acid at a ratio of 2:1–4:1. In this case the support is impregnated with a large quantity of water, while the quantity of the active agent remains low.

Through state-of-the-art solutions it has been possible to reduce the corrosion caused by formic acid. However, corrosion still causes financial losses and complicates the handling of the solutions. Owing to the high vapor pressure of formic acid, the handling of formic acid solutions is a problem even at low temperatures. The acid solutions are also quite corrosive.

SUMMARY OF THE INVENTION

An object of the present invention is to provide a product that contains as concentrated an amount as possible of the active agent, formic acid, but simultaneously have little corrosive action, and additionally the use of the product would be easy and safe.

Another object of the invention is to provide a method by which first a water-free formic acid can be ammoniated and then a solid product can be prepared.

By means of the present invention there is thus provided a product which has a reduced corrosive action and the handling of which is less hazardous to the environment than the handling of known products. The product contains partly neutralized water-free formic acid, which has a lower vapor pressure than non-ammoniated acid, whereby environmental hazards are reduced. Occupational hygiene is improved, since adverse odors and irritation are reduced.

According to one aspect, the present invention encompasses a solid antimicrobial product comprising: a concentrated formic acid partly neutralized with gaseous ammonia and having a water content less than 2% by weight absorbed in a support.

According to another aspect, the present invention encompasses a method for the production of a solid antimicrobial product, the method comprising forming a concentrated formic acid having a water content below 2% by weight, directing gaseous ammonia at the formic acid to render a formic acid to ammonium ion molar ratio of 3:1–38:1 and the partly neutralized formic acid, and contacting the partly neutralized formic acid with a support.

DETAILED DESCRIPTION OF THE INVENTION

A study of aqueous solutions of formic acid showed that aqueous acids are more corrosive than water-free formic acid. It was observed, unexpectedly, that by the use of a nearly water-free formic acid, having a water content below 2% by weight, it was possible to reduce corrosion considerably. In order to reduce corrosion, concentrated formic acid was further partly neutralized with gaseous ammonia, thus avoiding the passing of extra water into the product. In order to facilitate the handling of the product, the obtained ammoniated formic acid concentrate was absorbed into a support, causing as large an acid amount as possible to be absorbed into the support and at the same time reducing the amount of support. The solution according to the invention thus provides an additional advantage in cost saving, since supports as such are considerably more expensive than is formic acid itself. It has been possible to impregnate the same support amount with a maximum amount of active agent. At the same time the storage and transport costs have been reduced, since the product amounts/active agent are in a compact form.

The tests carried out also showed that the formic acid product according to the invention has a lower freezing point than has a non-neutralized water-free formic acid. This enables a liquid product to be transported and used at quite low temperatures even in winter without a risk of freezing. Likewise, the storage of the raw material is facilitated, since heated storage containers are not necessary.

The active agent in the product according to the invention is a nearly water-free formic acid. The water content of the formic acid must be below 2% by weight. Gaseous ammonia is used for the neutralization of the acid. The formic acid to ammonium ion molar ratio recommended for the solution thus obtained is 3:1–38:1, and an especially preferable range is 5:1–12:1. These ratios have been calculated on the basis of the chemical equivalents.

According to the invention, the partly ammoniated formic acid is absorbed into a support. The impregnation can be done, for example, by spraying the acid into a mechanically fluidized support. The support may be pulverous, porous or granulated. Both inorganic and organic inert support raw materials are suitable for use as the support. An inorganic support may be, for example, vermiculite, perlite, silica, alumina, clay, diatomite, or kaolin. An organic support may be, for example, soy powder, corn-cob fractions, a microbial protein, dried sugar cane pulp, or citrus tree pulp. The most important factors affecting the choice of the support include a high adsorption/absorption capacity and the absence of health hazards.

In the solid product according to the invention, the weight ratio of the formic acid to, the support is preferably within the range 0.25:1–9:1.

support via nozzles. The capacity of the apparatus was approximately 1 ton/h. The end product was a product containing partly ammoniated acid solution 70% by weight.

EXAMPLE 2

Corrosion tests were carried out as follows. Specimens prepared from carbon steel were immersed in vessels containing acid or partly neutralized acid, the vessels being equipped with a magnetic stirrer. In Table 1, notation FA denotes formic acid. The corrosion results were calculated from the change of weight of the specimens and from their surface area. The corrosion rate is indicated as corrosion rate mm/a.

TABLE I

| Specimen | FA % | Water % | $NH_3$ | Molar ratio acid:$NH_4$ | Vapor pressure mbar | Freezing point ° C. | Corrosion mm/a (Fe37 steel) | Note |
|---|---|---|---|---|---|---|---|---|
| 1 | 99 | 1 | 0 |  | 42.8 | +8 | 1.09 | State of the art |
| 2 | 98 | 1 | 1 | 38.4:1 | 38.6 | +6 | 0.40 | Invention |
| 3 | 96 | 1 | 3 | 12.5:1 | 31.3 | +1 | 0.76 | Invention |
| 4 | 94 | 1 | 5 | 7.4:1 | 25.1 | −6 | 0.71 | Invention |
| 5 | 92 | 1 | 7 | 5.2:1 | 19.9 | −13 | 0.78 | Invention |
| 6 | 90 | 1 | 9 | 3.9:1 | 15.6 | −19 | 0.90 | Invention |
| 7 | 95 | 5 | 0 |  | 37.8 | +2 | 3.68 | State of the art |
| 8 | 90 | 10 | 0 |  | 32.0 | −6 | 5.54 | State of the art |
| 9 | 85 | 15 | 0 |  | 27.0 | −12 | 5.72 | State of the art |

According to the invention, the partial neutralization of water-free formic acid is preferably carried out in a special reactor-cooler system. Gaseous ammonia is added under precisely controlled conditions, for example, via an ejector into a pressurized reactor that contains the water-free formic acid. Since the reaction is strongly exothermal, the solution must be cooled. This can be done advantageously, for example, by cycling the solution via an outside cooler back to the reactor. The temperature is maintained under control by controlling the ammonia fed in and by cooling the cycle. The final result obtained is a formic acid solution having the desired ammonium formate concentration.

The product according to the invention is suited for use as an antimicrobial agent for the preserving of an organic material and for combating detrimental microorganisms. An especially suitable use is the preservation or pH control (lowering) of feeds intended for animal consumption, such as complete feed, its components, green forage, soilage, and grain. Below, the invention is illustrated with examples.

EXAMPLE 1

A product was prepared as follows: 11,000 kg of a 99% formic acid was pumped into a pressure vessel having a volume of 10 m³. 780 kg of gaseous $NH_3$ was pumped into the solution while circulating the solution via a cycle and heat exchanger outside the reactor back to the reactor. The solution was cooled be means of cooling water in the heat exchanger. The intermediate product obtained was a solution in which the molar ratio of acid to ammonium ion was 5.2:1. The solid end product was prepared by spraying the ammoniated solution into a support in an apparatus wherein the support was fluidized by means of vigorous agitation. The impregnation was carried out continuously by feeding with a screw feeder the support (precipitated silica) into the mixer and by spraying the above-mentioned solution into the Specimens 2–6 represent partly neutralized formic acid compositions according to the invention. Respectively tests 1 and 7–9 represent state-of-the-art reference compositions.

In Table 1 the ratio has been calculated as the molar ratio of the formic acid used to the ammonium ion formed. The results show that the range most preferable in terms of corrosion is 38:1–5:1.

When the amount of ammonia is increased, corrosion initially drops sharply and thereafter rises slowly.

The vapor pressure decreases when the amount of ammonia is increased and is halved when the molar ratio of acid to ammonium ion is approximately 6:1.

The freezing point drops sharply when the amount of ammonia is increased, and already at a molar ratio of 12:1 it is below 0° C.

By the ammoniation of water-free or nearly water-free formic acid and by absorbing this into a support there is obtained a solid formic acid product having a low corrosion, less odor, and smaller environmental hazards. Ammoniation also lowers the freezing point, whereby the handling, transportation and storage of the liquid product is also facilitated before the absorption. When a water-free acid instead of an acid that contains water is used, the content of active agent in the obtained solid product is also high, and expensive support can be saved, in which case the product is more economical.

While the present invention has been described by reference to the above-mentioned embodiments, certain modifications and variations will be evident to those of ordinary skill in the art. Therefore, the present invention is to limited only by the scope and spirit of the appended claims.

What is claimed is:

1. A solid antimicrobial product comprising: a concentrated formic acid partly neutralized with gaseous ammonia and having a water content less than 2% by weight absorbed in a support.

2. The product according to claim 1, wherein the molar ratio of formic acid to ammonium ion is 3:1–38:1.

3. The product according to claim 1, wherein the molar ratio of formic acid to ammonium ion is 5:1–12:1.

4. The product according to claim 1, wherein the support is an inert inorganic or organic material.

5. The product according to claim 4, wherein the inorganic support is vermiculite, perlite, silica, alumina, clay, diatomite, or kaolin.

6. The product according to claim 4, wherein the organic support is soy powder, a microbial protein, dried sugar cane pulp, or citrus tree pulp.

7. The product according to claim 1, wherein the weight ratio of the formic acid to the support in the solid product is 0.25:1–9:1.

8. A method for the production of a solid antimicrobial product, the method comprising forming a concentrated formic acid having a water content below 2% by weight, directing gaseous ammonia at the formic acid to render a formic acid to ammonium ion molar ratio of 3:1–38:1 and the partly neutralized formic acid, and contacting the partly neutralized formic acid with a support.

9. The method according to claim 8, wherein the partly neutralized formic acid is sprayed into the support.

10. An organic material preservative and/or pH controller comprising the product of claim 1.

11. The preservative according to claim 10, wherein the organic material is an animal feed, a component of animal feed, green forage, soilage, or grain.

* * * * *